US008895042B2

(12) United States Patent
Mankovitz

(10) Patent No.: US 8,895,042 B2
(45) Date of Patent: Nov. 25, 2014

(54) NON-TOXIC AND ENVIRONMENTALLY COMPATIBLE PHOTO-PROTECTIVE PREPARATIONS

(76) Inventors: Roy J. Mankovitz, Montecito, CA (US); Kathleen Barry Mankovitz, legal representative, Montecito, CA (US)

( * ) Notice: Subject to any disclaimer, the term of this patent is extended or adjusted under 35 U.S.C. 154(b) by 0 days.

(21) Appl. No.: 13/582,575

(22) PCT Filed: Mar. 2, 2011

(86) PCT No.: PCT/US2011/026855
§ 371 (c)(1),
(2), (4) Date: Sep. 4, 2012

(87) PCT Pub. No.: WO2011/109505
PCT Pub. Date: Sep. 9, 2011

(65) Prior Publication Data
US 2012/0328674 A1 Dec. 27, 2012

Related U.S. Application Data

(60) Provisional application No. 61/309,575, filed on Mar. 2, 2010, provisional application No. 61/326,911, filed on Apr. 22, 2010, provisional application No. 61/364,168, filed on Jul. 14, 2010.

(51) Int. Cl.
| | |
|---|---|
| *A61K 8/02* | (2006.01) |
| *A61K 9/14* | (2006.01) |
| *A61Q 17/04* | (2006.01) |
| *A61K 8/19* | (2006.01) |
| *A61K 8/97* | (2006.01) |
| *A61K 8/40* | (2006.01) |
| *A61Q 19/00* | (2006.01) |

(52) U.S. Cl.
CPC .............. *A61Q 19/004* (2013.01); *A61Q 17/04* (2013.01); *A61K 8/19* (2013.01); *A61K 8/97* (2013.01); *A61K 8/40* (2013.01)
USPC ........................................... 424/401; 424/489

(58) Field of Classification Search
None
See application file for complete search history.

(56) References Cited

U.S. PATENT DOCUMENTS

| | | | |
|---|---|---|---|
| 1,999,160 A | 4/1935 | Walton | |
| 1,999,161 A | 4/1935 | Walton | |
| 2,414,024 A | 1/1947 | Cooper | |
| 4,284,630 A | 8/1981 | Yu et al. | |
| 4,882,143 A | 11/1989 | Kadokura et al. | |
| 5,968,528 A * | 10/1999 | Deckner et al. ................ | 424/401 |
| 6,037,289 A | 3/2000 | Chopin et al. | |
| 6,123,927 A | 9/2000 | Ogawa et al. | |
| 6,149,896 A * | 11/2000 | Riklis et al. ..................... | 424/59 |
| 6,274,152 B1 * | 8/2001 | Brieva et al. ................... | 424/401 |
| 6,528,072 B1 | 3/2003 | Williams et al. | |
| 6,783,754 B2 * | 8/2004 | Mankovitz ..................... | 424/59 |
| 6,805,875 B2 | 10/2004 | Bartels | |
| 2005/0261750 A1 | 11/2005 | McDaniel | |
| 2005/0266094 A1 | 12/2005 | Dinno | |
| 2006/0134026 A1 * | 6/2006 | Park et al. ..................... | 424/59 |
| 2006/0292094 A1 | 12/2006 | Bell | |
| 2007/0152201 A1 * | 7/2007 | Zhou et al. ................... | 252/609 |
| 2011/0117187 A1 * | 5/2011 | Stock et al. ................... | 424/450 |

OTHER PUBLICATIONS

Afaq, F. et al., Anthocyanin- and Hydrolyzable Tannin-Rich Pomegranate Fruit Extract Modulates MAPK and NF-kB Pathways and Inhibits Skin Tumorigenesis in CD-1 Mice, *Int. J. Cancer*, 113: 423-33, 2005.
Afaq, F. et al., Pomegranate Fruit Extract Modulates UV-B-mediated Phosphorylation of Mitogen-activated Protein Kinases and Activation of Nuclear Factor Kappa B in Normal Human Epidermal Keratinocytes, *Photochemistry and Photobiology*, 81: 38-45, 2005.
Afaq, F. et al., Delphinidin, an Anthocyanidin in Pigmented Fruits and Vegetables, Protects human HaCaT Keratinocytes and Mouse Skin Against UVB-Mediated Oxidative Stress and Apoptosis, *Journal of Investigative Dermatology*, 127: 222-32, 2007.
Alizadeh, A. et al., A study of the effect of magnesium hydroxide on the wound healing process in rats, Medical Journal of Islamic World Academy of Sciences, 16:(4): 165-170, 2007.
Calafat, A. et al., Concentrations of the Sunscreen Agent Benzophenone-3 in Residents of the United States: National Health and Nutrition Examination Survey 2003-2004, *Environmental Health Perspectives*, 116(7): 893-97, Jul. 2008.
Chalker-Scott, L., Environmental Significance of Anthocyanins in Plant Stress Responses, *Photochemistry and Photobiology*, 70(1): 1-9, 1999.
Cockell, C. et al., Ultraviolet radiation screening compounds, *Biol. Rev.*, 74: 311-45, 1999.
Duncan, F., The Effects of Black Raspberry Extract on UVB-Induced Inflammation and Carcinogenesis, Dissertation submitted to The Ohio State University, 2009.
Gibson, A. et al., The Use of Magnesium Hydroxide Slurry for Biological Treatment of Municipal and Industrial Wastewater, 2004.
Gitelson, A. et al., Optical Properties and Nondestructive Estimation of Anthocyanin Content in Plant Leaves, *Photochemistry and Photobiology*, 74(1): 38-45, 2001.
Gould, K., Role of Anthocyanins in Plant Photoprotection, University of Auckland, New Zealand (Date unknown; believed to have been published prior to filing date of application).
Gould, K., Nature's Swiss Army Knife: The Diverse Protective Roles of Anthocyanins in Leaves, Journal of Biomedicine and Biotechnology, 2004(5): 314-20, 2004.
Hoch, W. et al., Physiological significance of anthocyanins during autumnal leaf senescence, Tree Physiology, 21: 1-8, 2001.

(Continued)

*Primary Examiner* — Susan Tran
(74) *Attorney, Agent, or Firm* — Gifford, Krass, Sprinkle, Anderson & Citkowski, P.C.

(57) ABSTRACT

The present invention relates generally to methods and compositions for prophylaxis and treatment of skin conditions. Topical compositions which protect the skin from UV radiation damage and treat UV radiation damage done to the skin are provided according to embodiments of the present invention which include at least one cyanin derived from a plant and at least one additional agent selected from the group consisting of: a UV radiation reflector, a UV screening agent, niacinamide, and a combination of two or more thereof.

16 Claims, No Drawings

(56) References Cited

OTHER PUBLICATIONS (Author unknown), A review of the scientific literature on the safety of nanoparticulate titanium dioxide or zinc oxide in sunscreens, Australian Government, Dept. of Health and Ageing, Jan. 16, 2006.

Lafferty, M., Fighting cancer by the bramble; Scientists are hot to unlock the medicinal secrets of black raspberries, The Columbus (Ohio) Dispatch, May 22, 2007.

Nguyen, V. et al., Cytotoxic Effects of Bilberry Extract on MCF7-GFP-Tubulin Breast Cancer Cells, *Journal of Medicinal Food*, 13(2): 1-8, 2010.

Wang, L. et al., Anthocyanins and their role in cancer prevention, *Cancer Letters*, 269: 281-90, 2008.

Danovaro, R. et al., Sunscreens Cause Coral Bleaching by Promoting Viral Infections, *Environmental Health Perspectives*, 116(4): 441-447, Apr. 2008.

Wu, X. et al., Concentrations of Anthocyanins in Common Foods in the United States and Estimation of Normal Consumption, *J. Agric. Food Chem.*, 54: 4069-75, 2006.

(Author unknown) Black Raspberries Yield Possible Skin Cancer Treatment, Ohio State University Medical Center Press Release, Apr. 17, 2007.

Wu, J. et al., Magnesium hydroxide nanoparticles synthesized in water-in-oil microemulsions, *Journal of Colloid and Interface Science*, 324(1-2): 167-71, Aug. 2008 (Abstract only).

Pastorfide, G. et al., Zinc chloride spray—magnesium hydroxide ointment dual topical regimen in the treatment of obstetric and gynecologic incisional wounds, *Clinical Therapeutics*, 11(2): 258-63, Mar.-Apr. 1989 (Abstract only).

Duncan, F. et al., Topical treatment with black raspberry extract reduces cutaneous UVB-induced carcinogenesis and inflammation, *Cancer Prevention Research* (Phil., PA), 2: 665-72, 2009.

Wong, S. et al., Toxicities of nano zinc oxide to five marine organisms: influences of aggregate size and ion solubility, *Analytical and Bioanalytical Chemistry*, 396(2): 609-18, Jan. 2010 (Abstract only).

Brand, R. et al., Sunscreens containing physical UV blockers can increase transdermal absorption of pesticides, *Toxicology and Industrial Health*, 19(1): 9-16, Feb. 1, 2003 (Abstract only).

Brezova, V. et al., Reactive oxygen species produced upon photoexcitation of sunscreens containing titanium dioxide (an EPR study), *Journal of Photochemistry and Photobiology. B, Biology*, 79(2): 121-34, May 13, 2005 (Abstract only).

\* cited by examiner

NON-TOXIC AND ENVIRONMENTALLY COMPATIBLE PHOTO-PROTECTIVE PREPARATIONS

REFERENCE TO RELATED APPLICATIONS

This application claims priority from U.S. Provisional Patent Application Ser. Nos. 61/309,575, filed Mar. 2, 2010; 61/326,911, filed Apr. 22, 2010; and 61/364,168, filed Jul. 14, 2010, the entire content of all of which is incorporated herein by reference.

FIELD OF THE INVENTION

The present invention relates generally to methods and compositions for prophylaxis and treatment of skin conditions. According to specific aspects, the present invention relate to methods and compositions including plant-derived cyanins and/or mineral salts for prophylaxis and treatment of skin conditions.

BACKGROUND OF THE INVENTION

In my U.S. Pat. No. 6,783,754, Plant-Based Non-Toxic Sunscreen Products (incorporated herein by reference in its entirety), I disclosed plant-based non-toxic sunscreen preparations using cyanins derived from plants. Since the issuance of that patent, a variety of research studies have been conducted (including one self-funded university study) validating the efficacy of cyanins, particularly anthocyanins derived from fruit, in the role of a sunscreen, without toxicity to healthy skin cells. Such studies have been conducted using in vitro human skin cells, in vivo animal skin cells, and in vivo human skin cells.

During that same period, a variety of research studies have been conducted confirming that conventional sunscreens, using regulatory-approved organic- and mineral-based active ingredients, under many conditions are toxic to human skin cells. Some may be also be absorbed into the body and cause systemic illness. In addition, it has been shown that these same ingredients, when released into the environment, damage sensitive ecosystems, particularly marine ecosystems, including destruction of coral reefs.

While the role of cyanins in plants remains in debate, evidence has being gathering that they are involved in UV protection. Speculation includes their roles as an attenuator of UV energy, coupled with some sort of DNA repair mechanism. The effects of both mechanisms of UV protection appear to be concentration related.

To enjoy widespread consumer acceptance, skin preparations used for UV protection must meet certain cosmetic requirements (the look and feel), much of which is somewhat subjective. A classical example is that of zinc oxide. In its natural form, the white skin coloration is considered unacceptable, leading to the necessity to use micronized and nanoparticle versions of the compound.

SUMMARY OF THE INVENTION

Compositions for topical application to the skin of a subject are provided which include at least one cyanin derived from a plant and at least one additional agent for treatment or prophylaxis of a skin condition.

Topical compositions which protect the skin from UV radiation damage and treat UV radiation damage done to the skin are provided according to embodiments of the present invention which include at least one cyanin derived from a plant and at least one additional agent selected from the group consisting of: a UV radiation reflector, a UV screening agent, niacinamide, and a combination of two or more thereof.

Topical compositions which protect the skin from UV radiation damage and treat UV radiation damage done to the skin are provided according to embodiments of the present invention which include at least one cyanin derived from a plant and at least one mineral salt UV radiation reflector selected from the group consisting of: magnesium hydroxide, magnesium carbonate, calcium carbonate, dolomite and a combination of any two or more thereof.

Optionally, a mineral salt UV radiation reflector is included in compositions of the present invention as mineral salt particles having an average particle size in the range of about 1 nm-100 μm, inclusive.

Topical compositions which protect skin from UV radiation damage and treat UV radiation damage done to the skin are provided according to embodiments of the present invention which include at least one cyanin derived from a plant and at least one UV screening agent is selected from the group consisting of: para-aminobenzoic acid (PABA), avobenzone, cinoxate, dioxybenzone, ecamsule (terephthalylidene dicamphor sulfonic acid), homosalate, menthyl anthranilate, octocrylene, octyl methoxycinnamate, octyl salicylate, oxybenzone, padimate O, phenylbenzimidazole sulfonic acid, sulisobenzone, titanium dioxide, trolamine salicylate, zinc oxide and a combination of two or more thereof.

Topical compositions which protect the skin from UV radiation damage and treat UV radiation damage done to the skin are provided according to embodiments of the present invention which include at least one cyanin derived from a plant and niacinamide present in an amount in the range of about 1% to 5%, inclusive, by weight of the composition.

Optionally, a skin compatible carrier is included in a topical composition of the present invention.

Optionally, topical compositions according to the present invention are liposomal formulations.

Topical compositions which protect the skin from UV radiation damage and treat UV radiation damage done to the skin are provided according to embodiments of the present invention which include a mineral salt selected from the group magnesium hydroxide, magnesium carbonate, calcium carbonate, and dolomite; and a non-aqueous skin-compatible carrier, with the proviso that the topical composition excludes water, titanium dioxide and zinc oxide.

Topical compositions for treatment and/or prophylaxis of acne are provided according to embodiments of the present invention which include at least one cyanin derived from a plant and an anti-acne agent.

Topical compositions for treatment and/or prophylaxis of acne are provided according to embodiments of the present invention which include at least one cyanin derived from a plant and an anti-acne agent selected from the group consisting of: benzoyl peroxide, salicylic acid, resorcinol, alpha hydroxyl acids, and an anti-acne sulfur compound.

Topical compositions according to embodiments of the present invention include one or more cyanins derived from a plant in an amount in the range of about 0.1% to 60% by weight of the composition.

Optionally, a skin penetration enhancer is included in a topical composition of the present invention.

Topical compositions for bathing the skin of a subject are provided according to embodiments of the present invention which include at least one cyanin derived from a plant and at least one mineral salt selected from: a magnesium mineral salt, a zinc mineral salt, a potassium mineral salt, a selenium mineral salt, an iodine mineral salt and a combination of two or more thereof.

Topical compositions for bathing the skin of a subject are provided according to embodiments of the present invention which include at least one cyanin derived from a plant and at least one mineral salt selected from: magnesium sulphate, magnesium sulfate heptahydrate, magnesium chloride, zinc sulphate, potassium chloride, selenium sulfide, and potassium iodide.

Methods of treatment or prophylaxis of a skin condition are provided according to embodiments of the present invention which include applying at least one cyanin derived from a plant to the skin of a subject; and applying at least one additional agent for treatment or prophylaxis of the skin condition to the skin of the subject. Applying at least one cyanin derived from a plant to the skin of a subject is performed before, simultaneously, or after applying at least one additional agent for treatment or prophylaxis of the skin condition to the skin of the subject.

Methods are provided according to embodiments of the present invention to protect the skin from UV radiation damage and treat UV radiation damage done to the skin including applying at least one cyanin derived from a plant to the skin of a subject; and applying at least one additional agent of: a UV radiation reflector, a UV screening agent, niacinamide, and a combination of two or more thereof, to the skin of the subject. The at least one cyanin derived from a plant and the at least one additional agent are applied to the skin of the subject before, during or after exposure to UV radiation, such as UV radiation from the sun or from another source.

Methods are provided according to embodiments of the present invention to protect the skin from UV radiation damage and treat UV radiation damage done to the skin including applying at least one cyanin derived from a plant to the skin of a subject; and applying at least one mineral salt UV radiation reflector.

Methods are provided according to embodiments of the present invention to protect the skin from UV radiation damage and treat UV radiation damage done to the skin including applying at least one cyanin derived from a plant to the skin of a subject; and applying at least one mineral salt UV radiation reflector selected from the group consisting of: magnesium hydroxide, magnesium carbonate, calcium carbonate, dolomite and a combination of any two or more thereof.

Methods are provided according to embodiments of the present invention to protect the skin from UV radiation damage and treat UV radiation damage done to the skin including applying at least one cyanin derived from a plant to the skin of a subject; and applying at least one UV screening agent is selected from the group consisting of: para-aminobenzoic acid (PABA), avobenzone, cinoxate, dioxybenzone, ecamsule (terephthalylidene dicamphor sulfonic acid), homosalate, menthyl anthranilate, octocrylene, octyl methoxycinnamate, octyl salicylate, oxybenzone, padimate O, phenylbenzimidazole sulfonic acid, sulisobenzone, titanium dioxide, trolamine salicylate, zinc oxide and a combination of two or more thereof.

Methods are provided according to embodiments of the present invention for prophylaxis and treatment of acne including applying at least one cyanin derived from a plant to the skin of a subject; and applying an anti-acne agent.

Methods are provided according to embodiments of the present invention for prophylaxis and treatment of acne including applying at least one cyanin derived from a plant to the skin of a subject; and applying an anti-acne agent selected from the group consisting of: benzoyl peroxide, salicylic acid, resorcinol, alpha hydroxyl acids, and an anti-acne sulfur compound.

Methods are provided according to embodiments of the present invention which include applying at least one cyanin derived from a plant and applying at least one of: a magnesium mineral salt, a zinc mineral salt, a potassium mineral salt, a selenium mineral salt, and an iodine mineral salt, by bathing the skin of a subject in water including at least one cyanin derived from a plant and at least one of: a magnesium mineral salt, a zinc mineral salt, a potassium mineral salt, a selenium mineral salt, and an iodine mineral salt.

Methods are provided according to embodiments of the present invention which include applying at least one cyanin derived from a plant and applying at least one of: magnesium sulphate, magnesium sulfate heptahydrate, magnesium chloride, zinc sulphate, potassium chloride, selenium sulfide, and potassium iodide, by bathing the skin of a subject in water including at least one cyanin derived from a plant and at least one of: magnesium sulphate, magnesium sulfate heptahydrate, magnesium chloride, zinc sulphate, potassium chloride, selenium sulfide, and potassium iodide.

Topical compositions and methods for use on human skin are provided according to embodiments of the present invention which include magnesium hydroxide particles having an average particle size in the range of about 1 nm-100 μm. A skin-compatible carrier is optionally further included.

Topical compositions and methods for use on human skin are provided according to embodiments of the present invention which include liposomal magnesium hydroxide. A skin-compatible carrier is optionally further included.

Topical compositions and methods for use on human skin are provided according to embodiments of the present invention which include magnesium hydroxide particles, magnesium carbonate particles, calcium carbonate particles, dolomite particles, and a combination of any two or more thereof, the mineral salt particles having an average particle size in the range of about 1 nm-100 μm. A skin-compatible carrier is optionally further included.

Topical compositions and methods for use on human skin are provided according to embodiments of the present invention which include a liposomal mineral salt selected from the group liposomal magnesium hydroxide, liposomal magnesium carbonate, liposomal calcium carbonate, liposomal dolomite, and a combination of any two or more thereof. A skin-compatible carrier is optionally further included.

Topical compositions and methods for use on human skin are provided according to embodiments of the present invention which include a mineral salt selected from the group magnesium hydroxide, magnesium carbonate, calcium carbonate, and dolomite; and a non-aqueous skin-compatible carrier, with the proviso that the composition excludes water, titanium dioxide and zinc oxide.

Commercial packages are provided according to embodiments of the present invention which include a container containing at least one cyanin derived from a plant and a mineral salt selected from the group consisting of: a magnesium mineral salt, a zinc mineral salt, a potassium mineral salt, a selenium mineral salt, and an iodine mineral salt.

According to embodiments of the present invention, a container of the commercial package includes at least a first compartment and a second compartment, wherein both the first compartment and the second compartment have a wall defining an exterior of the container, an interior space, and an opening for passage of material between the interior space and the exterior of the container, wherein the first and the second compartment each contain at least one cyanin derived from a plant and a first mineral salt selected from the group consisting of: a magnesium mineral salt, a zinc mineral salt, a potassium mineral salt, a selenium mineral salt, and an iodine mineral salt, and wherein the mineral salt contained in the first compartment is different than the mineral salt contained in the second compartment.

DETAILED DESCRIPTION OF THE INVENTION

Compositions for topical application to the skin of a subject are provided which include at least one cyanin derived from a plant and at least one additional agent for treatment or prophylaxis of a skin condition.

The singular terms "a," "an," and "the" are not intended to be limiting and include plural referents unless explicitly state or the context clearly indicates otherwise.

As used herein, the term "cyanin" is defined as a family of compounds that includes anthocyanins, betacyanins and sugar-free derivatives known as cyanidins. The one or more cyanins derived from one or more plants included in compositions and methods of the present invention are provided as "cyanin-containing plant extracts" according to embodiments. The terms "cyanin-containing plant extracts" and "cyanin derived from a plant" are used interchangeably to refer to cyanins that are removed from their natural environment in cyanin-containing whole plants but does not necessarily implicate complete removal of other plant materials from the cyanins. Cyanin-containing plant extracts include about 1%-99% cyanins by weight of the total weight of the extract. Exemplary methods for extracting and purifying plant cyanins include those detailed in U.S. Pat. Nos. 4,211, 577; 4,302,200; 4,409,254; 5,089,410; and 6,783,754.

Topical compositions according to embodiments of the present invention include one or more cyanins derived from a plant in an amount in the range of about 0.1% to 60% by weight of the composition.

Topical compositions which protect the skin from UV radiation damage and treat UV radiation damage done to the skin are provided according to embodiments of the present invention which include at least one cyanin derived from a plant and at least one additional agent selected from the group consisting of: a UV radiation reflector, a UV screening agent, niacinamide, and a combination of two or more thereof.

Agents included in compositions and methods of the present invention, such as UV radiation reflectors, UV screening agents, niacinamide and anti-acne agents can be obtained from commercial sources, isolated from the natural environment or synthesized using well-known methodology.

Exact amounts of ingredients included in a topical composition to protect the skin from UV radiation damage and treat UV radiation damage of the present invention will depend on the desired characteristics of the composition, such as the desired Sun Protection Factor (SPF). SPF is a well-known measure of protection of skin against UV-light induced erythema. SPF of a particular composition can be tested in vitro and/or in vivo using well-known methods and devices.

In certain embodiments, the present invention provides topical compositions including one or more cyanins derived from one or more plants, a pH adjuster as needed, a suitable skin-compatible carrier and one or more mineral salts.

Mineral salts used in embodiments of compositions of the present invention include, but are not limited to, zinc oxide, titanium dioxide, magnesium hydroxide, magnesium carbonate, calcium carbonate, dolomite and a combination of two or more of these.

Topical compositions which protect the skin from UV radiation damage and treat UV radiation damage done to the skin are provided according to embodiments of the present invention which include at least one cyanin derived from a plant and at least one mineral salt UV radiation reflector selected from the group consisting of: magnesium hydroxide, magnesium carbonate, calcium carbonate, dolomite and a combination of any two or more thereof.

Embodiments of inventive topical compositions include 0.05-99% of one or more cyanins by weight of the total composition; 0.05-99% magnesium hydroxide, magnesium carbonate, calcium carbonate, dolomite or a combination of two or more of these by weight of the total composition; and a suitable skin-compatible carrier. Optionally, a pH adjuster is included.

Cyanins provide highly desirable attributes to topical photo-protective compositions. The mechanism(s) mediating the beneficial effects of cyanins are not fully characterized and there is evidence for UVA and UVB absorption, UVA and UVB reflection, antioxidant/free radical scavenger activity, anti-inflammatory activity and pro-apoptotic activity specific to DNA damaged cells. Cyanins can cause unwanted skin coloration in high concentration. In the case of anthocyanins, this manifests as a dark red or blue coloration. Cosmetic acceptability standards, which disfavor such skin coloration, provide a consumer defined upper limit to the concentration of cyanins in the preparations described in my earlier patent. This upper limit varies depending on the carrier and the skin characteristics of the user.

The present inventor has found that combining $Mg(OH)_2$ with plant-derived cyanins yields the unexpected benefit of increasing the concentration threshold for cyanins at which cosmetically undesirable skin coloration occurs. By way of example, the addition of magnesium hydroxide enabled an increase of anthocyanin concentration before noticeable skin coloration occurs, as compared with the preparation without $Mg(OH)_2$.

$Mg(OH)_2$ is recognized as non toxic, has wound healing properties, and has wide use in the oral preparation known as milk of magnesia.

As to the criteria that this added compound not be detrimental to the environment, magnesium hydroxide powder is used industrially as a non-hazardous alkali to neutralize acidic wastewaters. It also takes part in the Biorock method of building artificial reefs. Considering that many of the active components in conventional sunscreens pollute the marine environment and damage reefs, the characteristics of $Mg(OH)_2$ are remarkable indeed. One could speculate that its widespread use as a sunscreen ingredient could act to clean up the environmental damage caused by previous sunscreen preparations.

In addition to magnesium hydroxide, the present inventor has found that magnesium carbonate, calcium carbonate, and dolomite all perform the same function of enabling increased concentrations of cyanins in a sunscreen composition while maintaining a cosmetically acceptable preparation. Mixtures of magnesium hydroxide, magnesium carbonate, calcium carbonate, and dolomite also perform the same desirable functions. Additionally, all of these substances possess UV reflective properties, increasing the overall light attenuating characteristics of the final preparation, as compared to preparations that do not include the mineral salts. Magnesium carbonate, calcium carbonate, and dolomite are also non-toxic and compatible with the environment, since these mineral salts are not only part of the marine environment, but are actually the building block materials of coral reefs.

According to embodiments, the present invention provides topical compositions including one or more cyanins derived from one or more plants, a pH adjuster as needed, a suitable skin-compatible carrier and a mineral salt selected from magnesium hydroxide, magnesium carbonate, calcium carbonate, dolomite and a combination thereof. The topical compositions are applied to human skin before, during and/or after exposure to UV radiation to protect the skin from UV damage and/or to aid in treating UV damage to the skin. The improved topical compositions allow for application of cyanins at a higher concentration, while continuing to meet the cosmetic requirements, such as substantially no dark red or blue skin coloration due to the cyanins. Topical compositions of the present invention provide equivalent or better photo-protection compared to topical compositions including cyanins without one or more of the listed mineral salts. The provided topical compositions are non-toxic to the user and do not cause harm to the environment.

Since cyanins act to stop the reproduction of DNA damaged skin cells, while leaving healthy cells unharmed, they can, and have been, used alone for skin repair. However, the skin coloration problem limits the maximum concentration for cosmetic acceptability. Combinations of cyanins and mineral salts according to embodiments of the present invention solve the skin coloration problem, allowing higher cyanin concentrations, and thereby increasing the skin repair activity, completely independent of any sunscreen behavior. Thus, such preparations can be used for photoprotection as well as general skin care preparations such as night creams, eye creams, cleansers, cosmetic foundations and face and body moisturizers.

Optionally, a mineral salt UV radiation reflector is included in compositions of the present invention as mineral salt particles characterized by a defined average particle size. In particular embodiments, the included particles have a defined particle size distribution.

Included mineral salt particles have an average particle size in the range of about 1 nm-100 µm and can be any shape. According embodiments of the present invention, included mineral salt particles selected from magnesium hydroxide, magnesium carbonate, calcium carbonate, dolomite and combinations of two or more of these have an average particle size in the range of about 1 nm-100 µm. In particular embodiments, included mineral salt particles are nanoparticles and have an average particle size in the range of about 1 nm-1 µm. According embodiments of the present invention, included mineral salt particles selected from magnesium hydroxide, magnesium carbonate, calcium carbonate, dolomite and combinations of two or more of these have an average particle size in the range of about 1 nm-1 µm. In further embodiments, included mineral salt particles are microparticles and have an average particle size in the range of about 1 µm-100 µm. According embodiments of the present invention, included mineral salt particles selected from magnesium hydroxide, magnesium carbonate, calcium carbonate, dolomite and combinations of two or more of these have an average particle size in the range of about 1 µm-100 µm. Larger or smaller particles can be included depending on the particular composition.

Optionally, topical compositions according to the present invention are liposomal formulations. For example, it is contemplated that liposomal compositions including a mineral salt selected from magnesium hydroxide, magnesium carbonate, calcium carbonate, dolomite and combinations of two or more of these will be included in topical compositions of the present invention. Liposomes and emulsions are well-known types of pharmaceutical formulations. In embodiments of the present invention, liposomes are particles typically produced as a unilammellar bilayer or a multilammellar bilayer of amphipathic molecules enclosing an aqueous interior. Liposomes can include any type of amphipathic materials compatible with a composition to be delivered, illustratively including naturally-occurring lipids, synthetic lipids and combinations thereof. Preferably, non-toxic liposome ingredients are used, preferably derived from animal sources such as tallow and egg yolks. Included liposomes have an average particle size in the range of about 1 nm-100 µm. In particular embodiments, included liposomes have an average particle size in the range of about 1 nm-1 µm. In further embodiments, included liposomes have an average particle size in the range of about 1 µm-100 µm. In particular embodiments, the included liposomes have a defined particle size distribution. Liposomes, methods of their preparation and use are well-known in the art, as exemplified in L. V. Allen, Jr. et al., Ansel's Pharmaceutical Dosage Forms and Drug Delivery Systems, 8th Ed., Philadelphia, Pa.: Lippincott, Williams & Wilkins, 2005, pp. 663-666; and A. R. Gennaro, Remington: The Science and Practice of Pharmacy, Lippincott Williams & Wilkins, 21st ed., 2005, pp. 766-767.

During experimentation with the addition of mineral salts to cyanin-containing sunscreen compositions, it was discovered that magnesium hydroxide, magnesium carbonate, calcium carbonate, dolomite and combinations of two or more of these demonstrated effectiveness as a reflector of UV radiation over the UVA and UVB spectra even in the absence of cyanins. Thus, topical compositions according to embodiments of the present invention include a mineral salt selected from magnesium hydroxide, magnesium carbonate, calcium carbonate, dolomite and combinations of two or more of these and exclude cyanins. Such compositions further include a suitable skin-compatible carrier and, optionally, a pH adjuster.

The effectiveness of these mineral salts as reflectors of UV radiation in aqueous formulations excluding cyanins is believed to be concentration dependent. However, in conventional cosmetic preparations, the concentration of $Mg(OH)_2$ is usually limited to less than about 6%, since at higher concentrations, it tends to chalk out on the skin, leaving an undesirable white film. For applications where $Mg(OH)_2$ would be used alone (without cyanins) as a UV reflector, it may be desirable to employ increased concentrations above 6%, while eliminating chalking. It is anticipated that providing the mineral salts in the form of nanoparticles would enable higher concentrations without undesirable appearance. By way of example, in industrial applications where $Mg(OH)_2$ is being used as a flame retardant, research has been conducted into converting $Mg(OH)_2$ into nanoparticles. It is anticipated that such nanoparticles could be employed in a sunscreen, where concentrations higher than 6% would be achieved without the chalky appearance. Particle sizes in the low micron range may also achieve acceptable results. Thus, a non-toxic, environmentally compatible (and actually supportive) sunscreen can be derived using $Mg(OH)_2$, either in macro, micro, or nanoparticles sizes, as the active ingredient, combined with a suitable carrier that is also non-toxic to the user, and compatible with the environment.

Non-aqueous topical compositions are provided according to embodiments of the present invention which include a mineral salt selected from magnesium hydroxide, magnesium carbonate, calcium carbonate, dolomite and combinations of two or more of these. For example, non-aqueous formulations of inventive topical compositions include 0.1-99% magnesium hydroxide, magnesium carbonate, calcium carbonate, dolomite and combinations of two or more of these by weight of the total composition. In particular embodiments, the non-aqueous formulations exclude titanium dioxide, zinc oxide and water.

Further embodiments of the present invention include 0.05-99% of one or more cyanins by weight of the total composition (w/w); 0.05-25% of zinc oxide, titanium dioxide or both zinc oxide and titanium dioxide by weight of the total composition; and a suitable skin-compatible carrier. Optionally, a pH adjuster is included.

Included zinc oxide and/or titanium dioxide particles have an average particle size in the range of about 1 nm-100 μm and can be any shape. In particular embodiments, included zinc oxide and/or titanium dioxide particles are nanoparticles and have an average particle size in the range of about 1 nm-1 μm. In further embodiments, included zinc oxide and/or titanium dioxide particles are microparticles and have an average particle size in the range of about 1 μm-100 μm. Larger or smaller particles can be included depending on the particular composition. In particular embodiments, the included particles have a defined particle size distribution.

In some embodiments, zinc oxide and/or titanium dioxide are included in a non-nanoparticulate form in embodiments of compositions of the present invention. Non-nanoparticulate zinc oxide and titanium dioxide includes particles having an average particle size of 100 nm or greater and can be any shape. In further embodiments, non-nanoparticulate zinc oxide and titanium dioxide includes particles having an average particle size of 500 nm or greater. In still further embodiments, non-nanoparticulate zinc oxide and titanium dioxide includes particles having an average particle size of 1 micron or greater. Larger or smaller particles can be included depending on the particular composition. In particular embodiments, the included particles have a defined particle size distribution.

Compositions including cyanins and non-nanoparticulate zinc oxide and titanium dioxide provide a similar SPF with a reduced amount of zinc oxide and titanium dioxide compared to preparations containing zinc oxide and titanium dioxide without cyanins.

Topical compositions which protect skin from UV radiation damage and treat UV radiation damage done to the skin are provided according to embodiments of the present invention which include at least one cyanin derived from a plant and at least one UV screening agent. One or more UV reflecting mineral salts and/or niacinamide is optionally further included in such topical compositions.

The term "UV screening agent" is used herein to refer to substances typically included in conventional sunscreens which are characterized by absorption and/or reflection of UVA and/or UVB light.

UV screening agents include, but are not limited to para-aminobenzoic acid (PABA), avobenzone, cinoxate, dioxybenzone, ecamsule (terephthalylidene dicamphor sulfonic acid), homosalate, menthyl anthranilate, octocrylene, octyl methoxycinnamate, octyl salicylate, oxybenzone, padimate O, phenylbenzimidazole sulfonic acid, sulisobenzone, titanium dioxide, trolamine salicylate and zinc oxide. Embodiments of the present invention encompass compositions including two or more UV screening agents.

Embodiments of topical compositions of the present invention include 0.05-99% of one or more cyanins by weight of the total composition (w/w); 0.05-99% of a UV screening agent or a combination of two or more UV screening agents by weight of the total composition; and a suitable skin-compatible carrier. Optionally, a pH adjuster is included.

In particular embodiments, PABA can be included in amounts up to 15% w/w of the total weight of a sunscreen composition; avobenzone up to 3% w/w; cinoxate up to 3% w/w;
dioxybenzone up to 3% w/w; ecamsule up to 10% w/w; homosalate up to 15% w/w; menthyl anthranilate up to 5 percent w/w; octocrylene up to 10 percent w/w; octyl methoxycinnamate up to 7.5% w/w; octyl salicylate up to 5% w/w; oxybenzone up to 6% w/w; padimate O up to 8% w/w; phenylbenzimidazole sulfonic acid up to 4% w/w; sulisobenzone up to 10% w/w; titanium dioxide up to 25% w/w; trolamine salicylate up to 12% w/w; and zinc oxide up to 25% w/w.

It is believed that the combination of one or more cyanins and one or more UV screening agents in a topical composition of the present invention allows for a greater SPF than compositions containing the same concentration of the one or more UV screening agents without the one or more cyanins. Thus, a topical composition of the present invention achieves the same SPF as a conventional composition while including lower concentrations of UV screening agents.

Topical compositions which protect the skin from UV radiation damage and treat UV radiation damage done to the skin are provided according to embodiments of the present invention which include at least one cyanin derived from a plant and niacinamide. One or more UV reflecting mineral salts and/or one or more UV screening agents is optionally further included in such topical compositions.

Topical compositions which protect the skin from UV radiation damage and treat UV radiation damage done to the skin are provided according to embodiments of the present invention which include at least one cyanin derived from a plant and niacinamide present in an amount in the range of about 1% to 5%, inclusive, by weight of the composition.

It has been found by the present inventor that inclusion of small amounts of niacinamide, from 1 to 5% by weight of the total composition, results in a further decrease in the amount of erythema produced on human skin from standardized doses of UV radiation, as compared to the compositions without the niacinamide. As a result, SPF skin tests, which rely on erythema as a measure of efficacy, indicate higher SPF numbers for the niacinamide combinations. The SPF increase can be as much as ten points.

Skin Therapeutics

Topical compositions including one or more cyanins and an active ingredient for treatment of a skin condition or disorder are provided according to the present invention.

In particular embodiments, topical anti-acne compositions including one or more cyanins and one or more active ingredients for treatment of acne are provided according to the present invention.

There is a plethora of over-the-counter and prescription medications for the treatment of acne. The active ingredients for the non-prescription acne preparations typically include benzoyl peroxide, salicylic acid, resorcinol, alpha hydroxyl acids, and sulfur compounds. Most of these active ingredients cause undesirable side effects of irritation, inflammation, excessive drying of the skin, and photosensitivity.

In the present invention, it has been found that the inclusion of cyanin-containing plant extracts with these anti-acne active ingredients reduces the undesirable effects of treatment with these active ingredients, while not interfering with their efficacy. In particular, inflammation and redness are reduced, the time to heal is shortened, and the cyanins act as photoprotective agents as described above and in U.S. Pat. No. 6,783,754.

Topical compositions including one or more cyanins and an active ingredient for treatment of a skin condition or disorder include from about 0.1% to 30% cyanins, with the balance being one or more of the anti-acne active ingredients and skin-compatible carrier. Also, it is contemplated that a regulatory agency-approved sunscreen active ingredient, i.e. a UV screening agent, may be added to the preparation.

It has also been found by the present inventor that by combining one or more cyanins with one or more anti-acne active ingredients in a composition for treatment of acne, higher concentrations of the anti-acne active ingredients may be used without undue irritation. Such higher concentrations act to speed the anti-acne activity of the combination.

Another objective of an acne medication is to provide some indication to the user as to where the preparation has been applied to the skin, and where it has not. The deep color of plant cyanins can be used to effect in this instance, where it serves as an application guide to the user.

Formulations

Optionally, a skin compatible carrier is included in a topical composition of the present invention.

Formulations for topical administration according to embodiments of the present invention include, for example, ointments, lotions, creams, gels, serums, pastes, sprays and powders. Ointments, lotions, creams, gels and pastes can include, in addition to one or more active agents, a base such as an absorption base, water-removable base, water-soluble base or oleaginous base and excipients such as one or more thickening agents, skin penetration enhancers, gelling agents, colorants, stabilizers, emulsifying agents, suspending agents, and perfuming agents.

Powders and sprays for topical administration can include excipients such as talc, lactose and one or more silicic acids. Sprays can include a pharmaceutical propellant such as a fluorinated hydrocarbon propellant, carbon dioxide, or a suitable gas. Alternatively, a spray can be delivered from a pump-style spray device which does not require a propellant. A spray device delivers a metered dose of a composition contained therein, for example, using a valve for regulation of a delivered amount.

A composition of the present invention is optionally formulated as a serum. The term "serum" has been in use in cosmetology for about 20 years. The term "serum" refers to a water-or oil-based preparation that is highly concentrated in its active ingredients, and is designed to be applied to the skin prior to the use of any other topical skincare or cosmetic compound. One embodiment of compositions of the present invention useful in connection with photo-protection includes a serum formulation containing one or more cyanins in a concentration from 0.1% to 60% by weight of the formulation, a skin-compatible carrier designed for rapid skin penetration, and, optionally, one or more pH adjustors.

Excipients for topical compositions are well-known in the art, for example as detailed in L. V. Allen, Jr. et al., Ansel's Pharmaceutical Dosage Forms and Drug Delivery Systems, 8th Ed., Philadelphia, Pa.: Lippincott, Williams & Wilkins, 2005; A. R. Gennaro, Remington: The Science and Practice of Pharmacy, Lippincott Williams & Wilkins, 21st ed., 2005, and J. G. Hardman et al., Goodman & Gilman's The Pharmacological Basis of Therapeutics, McGraw-Hill Professional, 10th ed., 2001.

A skin-compatible carrier designed for rapid skin penetration includes a skin penetration enhancer, according to embodiments of the present invention. Skin penetration enhancers, also known as absorption promoters, are well-known excipients with a variety of mechanisms of action which improve percutaneous absorption. Skin penetration enhancers are exemplified by, but not limited to, dimethyl sulfoxide, ethanol, propylene glycol, glycerin, polyethylene glycol, urea, dimethyl acetamide, sodium lauryl sulfate, poloxamers, Spans, Tweens, lecithin and terpenes.

To meet non-toxic criteria for a sunscreen carrier, the candidates are preferably restricted to compounds that can be used in their natural state, that do not degrade when exposed to UV radiation, that are compatible with human skin, and not detrimental to the environment. Edible plant oils that are preferably dominant in saturated fats are chosen for their stability. The tropical oils of coconut, palm fruit and palm nut are acceptable. Oils containing more than 10% polyunsaturated fatty acids were eliminated as too unstable in the UV environment. Olive oil, chosen with a monounsaturated fatty acid profile of at least 80 percent, is also acceptable for blending with the tropical oils up to a maximum of 25 percent of the oil combination. Animal fats such as beef tallow are also acceptable.

If it is desired to add a preservative to the topical compositions, again the criteria on non-toxicity to the user, and environmental compatibility are applied. A preservative that meets this criteria is iodine, which is an essential mineral for the human body (many people are deficient), and is found in large concentrations in sea vegetables such as kelp and seaweed. It is also a natural element in seawater. Concentrations in the range of 0.01 percent should prove adequate.

Topical compositions of the present invention have a pH compatible with human skin, generally in the range of about pH 5-pH 8. One or more pH adjustors is included in a composition of the present invention, if needed, to bring the composition to a desired pH.

In formulations including a pH adjuster, an acidifying agent may be used to adjust the pH of the formulation to match the slightly acidic nature of the skin. In that regard, citric acid is an acidifier of choice, being derived from fruits. It is also a well known additive to a variety of foods and is non-toxic to the user and compatible with the environment.

Bath Formulations

Topical compositions are provided according to embodiments of the present invention which are formulated for use while bathing.

Topical compositions for bathing the skin of a subject are provided according to embodiments of the present invention which include at least one cyanin derived from a plant and at least one mineral salt selected from: a magnesium mineral salt, a zinc mineral salt, a potassium mineral salt, a selenium mineral salt, an iodine mineral salt and a combination of two or more thereof.

Topical compositions for bathing the skin of a subject are provided according to embodiments of the present invention which include at least one cyanin derived from a plant and at least one mineral salt selected from: magnesium sulphate, magnesium sulfate heptahydrate, magnesium chloride, zinc sulphate, potassium chloride, selenium sulfide, and potassium iodide.

A variety of bath water preparations are marketed, promising health enhancements to the user simply by adding the preparations to bath water. Many of them include bath salts, such as sea salt, Epsom salt, and such, which contain essential minerals for the body that are absorbed through the skin. However, the amount of absorption is generally quite low, and some of the salts can irritate the skin, limiting the amount that can be used at any one time.

It has been found by the present inventor that combining bath salts with one or more plant cyanins increases the amount of absorption, and reduces skin irritation compared to use of bath salts alone. Accordingly, higher concentrations of salts than are conventionally used can be employed in the combination with an overall improved bathing experience. Further, as indicated above, topically applied cyanins provide skin photo-protection. By allowing the cyanins to penetrate the skin in a bath, it is anticipated that the photo-protective effects will last for several hours after the bath. The cyanin concentration in the bath salt preparation ranges from 0.1% to 60% by weight.

It has also been found that a bathing regimen where a single mineral salt is used for each bath, rather than a mineral combination, enhances absorption. Thus, in order to provide a spectrum of mineral baths, it is desirable to take a sequence of baths, where each employs a different mineral salt. The sequence may be a daily rotation, or weekly. By way of example, it is contemplated that magnesium, zinc, potassium, selenium, and iodine salts, each combined with one or more cyanins, would be provided as a kit for use in a five-bath regimen, each taken separately.

For magnesium, magnesium sulphate (such as magnesium sulfate heptahydrate, Epsom salt) or magnesium chloride are likely salt candidates. For zinc, zinc sulphate can be used; for potassium, potassium chloride; for selenium, selenium sulfide; and for iodine, potassium iodide.

The amount of each salt included with the one or more cyanins in a bath can vary depending on the salt, the amount of time the user will be exposed to the salt in the bath and the desired result. In general, the amount of added mineral salt will have a final concentration in the range of about $1 \times 10^{-5}\%$-10% in the bathwater, although the amount added to bathwater can be higher or lower.

In particular embodiments, to ensure that an excess is not absorbed, the total mineral amount in each bath packet might be limited to the Recommended Daily Allowance, as set by the FDA. Thus, for magnesium it might be 300 mg; for zinc, 25 mg, and so on.

In order to assist the user to keep track of the sequence of mineral baths, it is contemplated that the group of bath salts would be packaged in a single container having multiple compartments, each containing a quantity of one mineral salt with a cyanin. A typical single bath quantity might be 8 ounces of the combination. The package would contain a spout mounted to a rotating cover, whereby as the cover is rotated, the spout sequentially communicates with one of the multiple compartments. The cover can be designed so that it can only be rotated in one direction, to aid the user in selecting the individual salts in a mono-sequence.

Methods

Methods of protecting human skin from ultraviolet light (UV) and/or treating skin damage due to exposure to UV light are provided according to the present invention which included applying a topical composition described herein to human skin. The topical composition can be applied with effect before, during and/or after exposure to UV radiation.

Methods of treatment or prophylaxis of a skin condition are provided according to embodiments of the present invention which include applying at least one cyanin derived from a plant to the skin of a subject; and applying at least one additional agent for treatment or prophylaxis of the skin condition to the skin of the subject. Applying at least one cyanin derived from a plant to the skin of a subject is performed before, simultaneously, or after applying at least one additional agent for treatment or prophylaxis of the skin condition to the skin of the subject.

The terms "treating," "treatment" and grammatical equivalents are used herein to refer to administration of a composition of the present invention to a subject who has a sign or symptom of a skin condition, to inhibit or ameliorate the skin condition present in a subject, such as slowing progression of the condition and/or reducing or ameliorating a sign or symptom of the condition. The terms "prophylaxis," "prophylactic," "protective" and grammatical equivalents are used herein to refer to administration of a composition of the present invention to a subject who does not yet display a sign or symptom of a skin condition but who is at risk for the skin condition, to inhibit or ameliorate the skin condition in a subject, such as slowing progression of the condition and/or reducing or ameliorating a sign or symptom of the condition.

The term "skin condition" as used herein broadly refers to any condition of the skin in need of treatment or prophylaxis, including, but not limited to, acute effects of exposure to UV light, chronic effects of exposure to UV light, acne and inflammation.

Signs and symptoms of skin exposure to UV light include, but are not limited to, erythema, swelling and blistering of the affected skin. Signs and symptoms of the effects of acne on the skin include, but are not limited to, inflammation and pustular lesions.

Methods are provided according to embodiments of the present invention to protect the skin from UV radiation damage and treat UV radiation damage done to the skin including applying at least one cyanin derived from a plant to the skin of a subject; and applying at least one additional agent selected from the group consisting of: a UV radiation reflector, a UV screening agent, niacinamide, and a combination of two or more thereof, to the skin of the subject. The at least one cyanin derived from a plant and the at least one additional agent are applied to the skin of the subject before, during or after exposure to UV radiation, such as UV radiation from the sun or from another source.

Methods are provided according to embodiments of the present invention to protect the skin from UV radiation damage and treat UV radiation damage done to the skin including applying at least one cyanin derived from a plant to the skin of a subject; and applying at least one mineral salt UV radiation reflector. Such methods further optionally include applying at least one UV screening agent and/or niacinamide.

Methods are provided according to embodiments of the present invention to protect the skin from UV radiation damage and treat UV radiation damage done to the skin including applying at least one cyanin derived from a plant to the skin of a subject; and applying at least one mineral salt UV radiation reflector selected from the group consisting of: magnesium hydroxide, magnesium carbonate, calcium carbonate, dolomite and a combination of any two or more thereof.

Methods are provided according to embodiments of the present invention to protect the skin from UV radiation damage and treat UV radiation damage done to the skin including applying at least one cyanin derived from a plant to the skin of a subject; and applying at least one UV screening agent. Such methods further optionally include applying at least one mineral salt and/or niacinamide.

Methods are provided according to embodiments of the present invention to protect the skin from UV radiation damage and treat UV radiation damage done to the skin including applying at least one cyanin derived from a plant to the skin of a subject; and applying at least one UV screening agent selected from the group consisting of: para-aminobenzoic acid (PABA), avobenzone, cinoxate, dioxybenzone, ecamsule (terephthalylidene dicamphor sulfonic acid), homosalate, menthyl anthranilate, octocrylene, octyl methoxycinnamate, octyl salicylate, oxybenzone, padimate O, phenylbenzimidazole sulfonic acid, sulisobenzone, titanium dioxide, trolamine salicylate, zinc oxide and a combination of two or more thereof. Such methods further optionally include applying at least one mineral salt and/or niacinamide.

Methods are provided according to embodiments of the present invention to protect the skin from UV radiation damage and treat UV radiation damage done to the skin including applying at least one mineral salt selected from the group consisting of: magnesium hydroxide, magnesium carbonate, calcium carbonate, dolomite and a combination of any two or more thereof.

Methods are provided according to embodiments of the present invention to protect the skin from UV radiation damage and treat UV radiation damage done to the skin including applying at least one cyanin derived from a plant to the skin of a subject; and applying zinc oxide, titanium dioxide or both zinc oxide and titanium dioxide. Such methods further optionally include applying one or more of: at least one UV screening agent, at least one mineral salt and niacinamide.

Methods are provided according to embodiments of the present invention which include applying at least one cyanin derived from a plant and applying at least one of: a magnesium mineral salt, a zinc mineral salt, a potassium mineral salt, a selenium mineral salt, and an iodine mineral salt, by bathing the skin of a subject in water including at least one cyanin derived from a plant and at least one of: a magnesium mineral salt, a zinc mineral salt, a potassium mineral salt, a selenium mineral salt, and an iodine mineral salt.

Methods are provided according to embodiments of the present invention which include applying at least one cyanin derived from a plant and applying at least one of:

magnesium sulphate, magnesium sulfate heptahydrate, magnesium chloride, zinc sulphate, potassium chloride, selenium sulfide, and potassium iodide, by bathing the skin of a subject in water including at least one cyanin derived from a plant and at least one of: magnesium sulphate, magnesium sulfate heptahydrate, magnesium chloride, zinc sulphate, potassium chloride, selenium sulfide, and potassium iodide.

Topically applied cyanins have both anti-inflammatory as well as skin repair characteristics, and it is believed that such characteristics are not only dose dependent, but time dependent. That is, the longer they are in contact with skin cells, the more effective their desirable effects will be apparent. Therefore, one embodiment of the use of topical cyanins in connection with photo-protection includes 1) application of a serum formulation containing one or more cyanins in a concentration from 0.1% to 60% by weight of the formulation, a skin-compatible carrier designed for rapid skin penetration, and, optionally, one or more pH adjustors; and 2) application of a sunscreen preparation containing, for example, one of the approved organic or mineral UV screening agent active ingredients disclosed above. Thus, methods are provided which dispose the one or more cyanins in contact with skin cells prior to and/or during exposure to UV radiation. Further, the serum can be reapplied after exposure, and after the sunscreen has been washed off the skin. This enables the cyanin to continue its desirable effects for say, 48 hours after exposure, during the time when erythema normally takes place from excessive UV exposure.

While topical compositions and methods of the present invention are described herein primarily with regard to use for protection of human skin from ultraviolet light, it is appreciated that compositions and methods of the present invention can also be used in conjunction with non-human animals such as dogs, cats, pigs and other animals sensitive to detrimental effects of exposure to ultraviolet light.

Methods are provided according to embodiments of the present invention for prophylaxis and treatment of acne including applying at least one cyanin derived from a plant to the skin of a subject; and applying an anti-acne agent.

Methods are provided according to embodiments of the present invention for prophylaxis and treatment of acne including applying at least one cyanin derived from a plant to the skin of a subject; and applying an anti-acne agent selected from the group consisting of: benzoyl peroxide, salicylic acid, resorcinol, alpha hydroxyl acids, and an anti-acne sulfur compound.

Commercial Packages

Commercial packages are provided according to embodiments of the present invention which include at least one topical composition described herein along with instructions for use thereof. Commercial packages are provided according to embodiments of the present invention which include at least one topical composition described herein and a conventional sunscreen, along with instructions for use thereof.

Embodiments of inventive compositions and methods are illustrated in the following examples. These examples are provided for illustrative purposes and are not considered limitations on the scope of inventive compositions and methods.

EXAMPLE

Three compositions were prepared: 1) zinc oxide (5% by weight)+coconut oil; 2) zinc oxide (25% by weight)+coconut oil; and 3) zinc oxide (5% by v)+coconut oil+bilberry extract (5% by weight) The bilberry extract used was standardized for 25% by weight anthocyanin content.

Equivalent amounts of each composition were applied evenly to the skin of a subject and exposed to full noontime sunlight for two hours. Following sun exposure, the compositions are removed from the skin which is evaluated for erythyma. No skin redness (erythema) was noticed under the area for preparations 2 and 3, while there was noticeable redness for the uncovered portion of the arm and for the area under preparation 1. Results show that the bilberry extract provided significant UV protection, even with a reduced amount of zinc oxide.

Any patents or publications mentioned in this specification are incorporated herein by reference to the same extent as if each individual publication is specifically and individually indicated to be incorporated by reference.

The compositions and methods described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims.

The invention claimed is:

1. A topical composition for use on human skin, comprising:
   at least one cyanins derived from a plant;
   and magnesium hydroxide,
   wherein the magnesium hydroxide is in the form of particles having an average particle size in the range of about 1 nm-100 μm, and
   wherein the composition comprises 0.05-99% of the at least one cyanins, and 0.05-99% of the magnesium hydroxide by weight of the total composition.

2. The topical composition of claim 1, further comprising a UV screening agent is selected from the group consisting of: para-aminobenzoic acid (PABA), avobenzone, cinoxate, dioxybenzone, ecamsule (terephthalylidene dicamphor sulfonic acid), homosalate, menthyl anthranilate, octocrylene, octyl methoxycinnamate, octyl salicylate, oxybenzone, padimate O, phenylbenzimidazole sulfonic acid, sulisobenzone, titanium dioxide, trolamine salicylate, zinc oxide and a combination of two or more thereof.

3. The topical composition of claim 1, further comprising niacinamide present in an amount in the range of about 1% to 5%, inclusive, by weight of the composition.

4. The topical composition of claim 1, further comprising an anti-acne agent selected from the group consisting of: benzoyl peroxide, salicylic acid, resorcinol, alpha hydroxyl acids, and an anti-acne sulfur compound.

5. The topical composition of claim 1, further comprising a skin compatible carrier.

6. The topical composition of claim 1, wherein the cyanin, magnesium hydroxide or a combination of the cyanin and the magnesium hydroxide is a liposomal formulation of the cyanin, the magnesium hydroxide or the combination of the cyanin and the magnesium hydroxide.

7. The topical composition of claim 5, wherein the carrier is a non-aqueous skin-compatible carrier, with the proviso that the topical composition excludes water, titanium dioxide and zinc oxide.

8. The topical composition of claim 1, wherein the one or more cyanins is present in an amount in the range of about 0.1% to 60% by weight of the composition.

9. The topical composition of claim 1, further comprising a skin penetration enhancer.

10. The topical composition of claim 1, further comprising a mineral salt selected from: magnesium sulphate, magnesium sulfate heptahydrate, magnesium chloride, zinc sulphate, potassium chloride, selenium sulfide, and potassium iodide.

11. A method of treatment or prophylaxis of a skin condition, comprising:
applying the composition of claim 1 to the skin of a subject.

12. The method of claim 11 wherein the subject has, or is at risk of having, UV radiation damage and wherein the composition is applied to the skin of the subject before, during or after exposure to UV radiation.

13. The method of claim 11 wherein applying the composition of claim 1 comprises bathing the skin of the subject in water comprising the composition.

14. A commercial package, comprising:
a container containing the composition of claim 1.

15. The topical composition of claim 1, wherein the composition has a pH in the range of pH 5- pH 8.

16. The topical composition of claim 1, formulated as an ointment, lotion, cream, gel, serum, powder, paste or spray.

* * * * *